United States Patent [19]
Frey

[11] 3,994,585
[45] Nov. 30, 1976

[54] OPTO-ELECTRICAL MEASURING APPARATUS FOR DETERMINING THE RELATIVE HEMOGLOBIN CONTENT OF AN ILLUMINATED SOLUTION BY EVALUATING ITS LIGHT ABSORPTION

[75] Inventor: Raymond Frey, Zurich, Switzerland

[73] Assignee: Contraves AG, Zurich, Switzerland

[22] Filed: Aug. 11, 1975

[21] Appl. No.: 603,547

[30] Foreign Application Priority Data
Aug. 20, 1974 Switzerland.................... 11328/74

[52] U.S. Cl.............................. 356/40; 356/184; 356/206; 356/222
[51] Int. Cl.² ...................... G01N 33/16; G01J 3/48; G01N 21/22
[58] Field of Search .............................. 356/40–42, 356/206, 222, 229, 230, 184–185; 250/565

[56] References Cited
UNITED STATES PATENTS

| | | | |
|---|---|---|---|
| 2,042,281 | 5/1936 | Traver | 356/206 |
| 2,051,320 | 8/1936 | States | 356/41 |
| 2,382,220 | 8/1945 | Fogle | 356/222 |
| 2,481,567 | 9/1949 | Brown | 356/41 |
| 3,544,222 | 12/1970 | Jannasch et al. | 356/206 |

Primary Examiner—John K. Corbin
Assistant Examiner—Wm. H. Punter
Attorney, Agent, or Firm—Werner W. Kleeman

[57] ABSTRACT

An opto-electrical measuring apparatus for determining the hemoglobin content of an illuminated hemoglobin solution arranged in the path of light between a light source and a photoelectric transducer by evaluating the light absorption of the solution within a predetermined wavelength range. The spectral or spectrum properties of the light source, the transducer and other components arranged in the path of the light emanating from the light source are accommodated or matched to one another such that in the absence of the hemoglobin solution in the path of light an electrical magnitude generated in the photoelectric transducer possesses a spectral dependency which in the wavelength range of 540 to 560 nm constitutes a maximum value and to both sides of such range with a half-value width of at least 60 nm continually decreases to less than 20% of the maximum value at about 500 and 600 nm, respectively, and externally of these band limits asymptotically approaches the value null.

7 Claims, 6 Drawing Figures

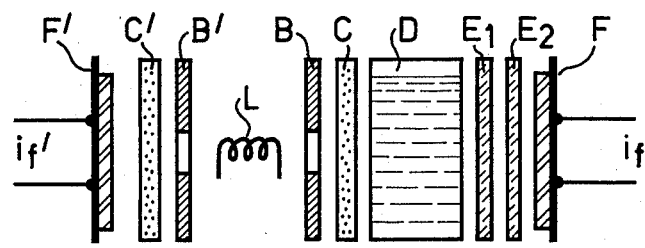
FIG. 1
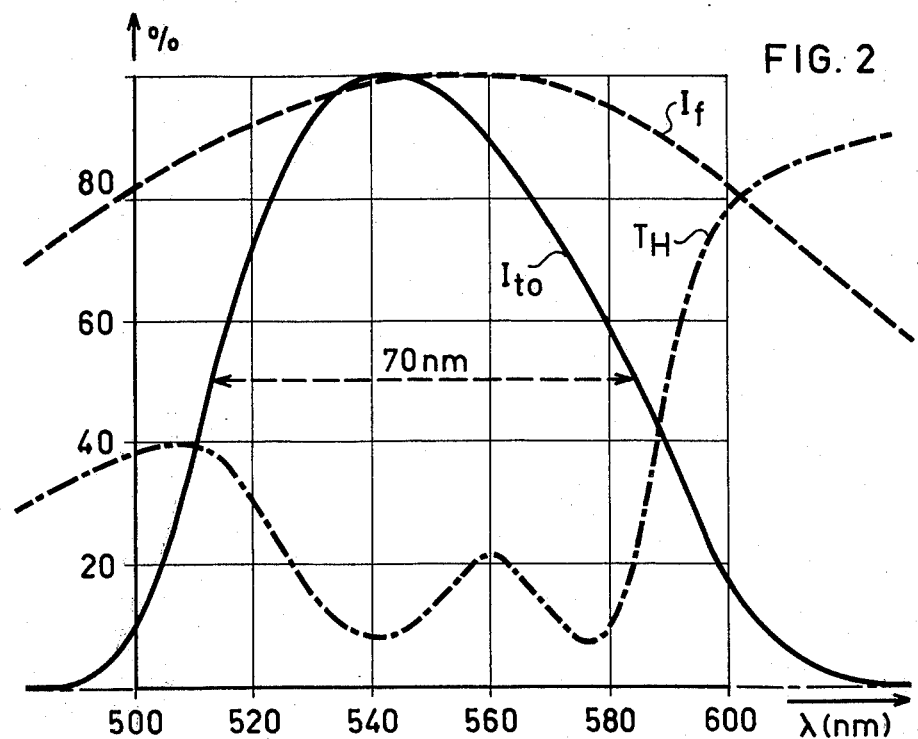
FIG. 2
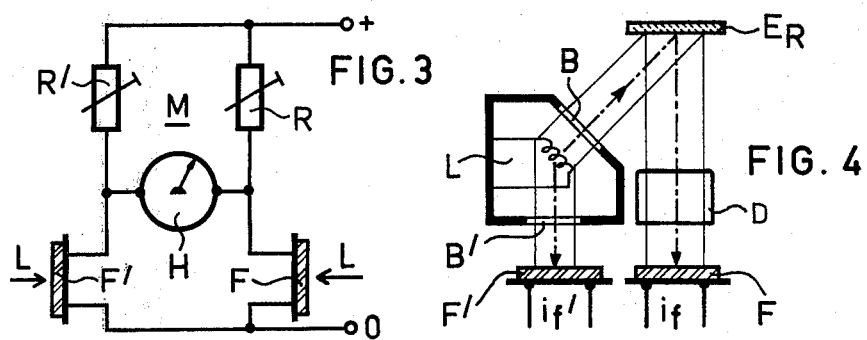
FIG. 3
FIG. 4

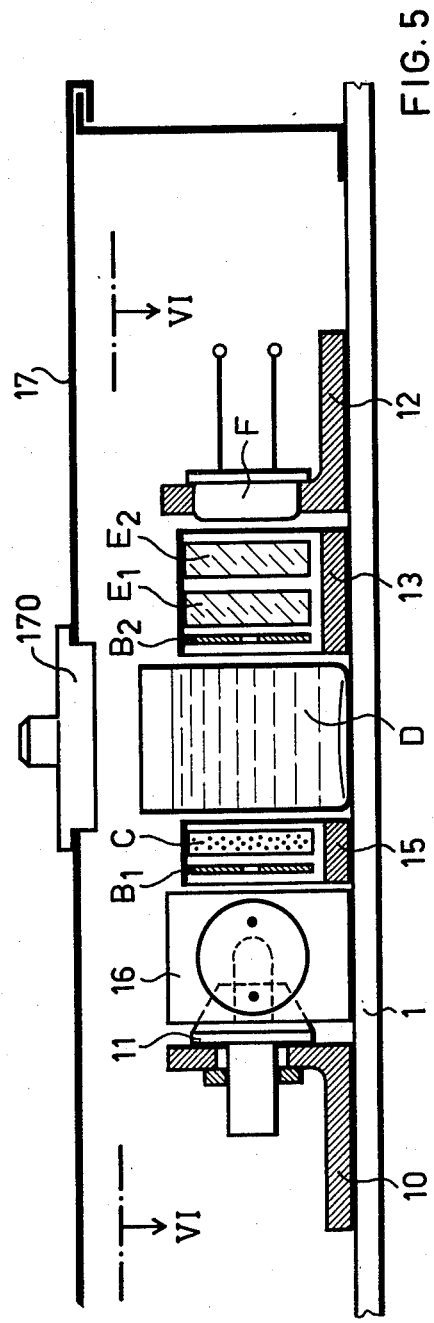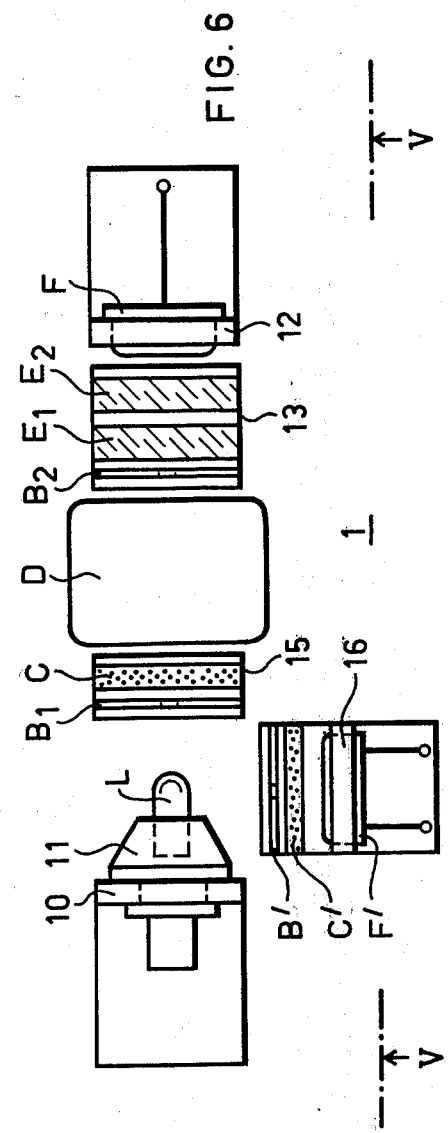

OPTO-ELECTRICAL MEASURING APPARATUS FOR DETERMINING THE RELATIVE HEMOGLOBIN CONTENT OF AN ILLUMINATED SOLUTION BY EVALUATING ITS LIGHT ABSORPTION

BACKGROUND OF THE INVENTION

The present invention relates to a new and improved construction of an opto-electrical measuring apparatus for determining the relative hemoglobin content of an illuminated hemoglobin solution arranged in the path of light between a light source and a photoelectric transducer by evaluating the light absorption thereof over a predetermined wavelength range.

Such type measuring devices have become known for instance from the following publications:

a. S. M. LEWIS: "International Standard for Hemoglobinometry"
J. clin. path (1967) 20.791 b. O. W. van ASSENDELFT: "Photometry and the Standardized Method for the Determination of Haemoglobin"
Schweiz. med. Wochenschr. 101.1649–1652 (1971)

c. O. W. van ASSENDELFT: "Spectrometry of Haemoglobin Derivatives"
Verlag: Royal VANGORCUM LTD., Assen NL (1970) According to such heretofore known standard procedures there is evaluated from the available light spectrum only a narrow wavelength band which is at a maximum at $\lambda = 540$ nm (1 nm $=10^{-9}$m) and a half-width or half-value width of not more than 20 nm, for instance by the spectral resolution of the light emanating from an illuminated slot or by inserting a suitable narrow band transmission-color filter in the light path.

Since for the determination of the total hemoglobin content there must be taken into account a number of hemoglobin derivatives, namely, Hb, $HbO_2$ and HbCO, the transmission characteristics of which at $\lambda = 540$ nm are different from one another, in order to be able to use the heretofore known standard measurement or measuring devices it is necessary to add to the haemolyse or hemoglobin solution a cyanogen-containing reaction solution in order to transform all hemoglobin derivatives into a uniform chemical compound (the so-called cyanment-method).

The use of cyanogen-containing and corresponding poisonous reaction solutions for the preparation of the hemoglobin solution which is to be examined is oftentimes associated with considerable danger when the examination of the blood is carried out by relatively unskilled hospital or clinical attendants, i.e. people who do not possess too great medical training and furthermore, requires the expiration of a reaction time amounting to a number of minutes. Thus, the leukocytes contained in the solution are also damaged, something oftentimes undesired. Additionally, a narrow band light utilization for photometric examination devices requires, for reasons of energy, the presence of relatively complicated slot illumination and imaging optical systems.

SUMMARY OF THE INVENTION

Hence, it is a primary object of the present invention to provide an improved apparatus of the character described which is not associated with the aforementioned drawbacks and limitations of the prior art proposals.

Another and more specific object of the present invention aims at the provision of an improved hemoglobin measuring apparatus which, according to the heretofore initially set forth subject matter of invention, likewise evaluates the light absorption of a hemoglobin solution over a predetermined wavelength range, but in a wide band range instead of a narrow band range, namely over the entire wavelength range of 500 to 600 nm, in such a manner that without the need for the transformation of the different hemoglobin derivatives into a uniform chemical compound or composition by the addition of poisonous reaction substances and without the need to use auxiliary optical aids for the bundling of the light and resolution thereof there can be produced an indicator magnitude which corresponds as linearly as possible to the total hemoglobin content of the solution.

The invention is based upon the recognition that the most important hemoglobin derivatives Hb, $HbO_2$ and HbCO contained in a solution with the same concentration bring about an approximately equal integral-absorption if there is selectively utilized the light wavelength range of 500 to 600 nm. Consequently, the absorption of a mixture of such derivatives is independent of the relative composition and is therefore a direct measure for the total hemoglobin concentration.

Now in order to implement the foregoing objects, and others which will become more readily apparent as the description proceeds, the opto-electrical measuring apparatus of the previously mentioned type is generally manifested by the features that the spectral properties of the light soure, the transducer and the remaining components arranged in the path of light are accommodated or matched to one another in such a manner that in the absence of the hemoglobin solution in the light path an electrical magnitude produced in the photoelectric transducer exhibits a spectral dependency which in the wavelength range of 540 to 560 nm constitutes a maximum and to both sides of such range with a half-value width or at least 60 nm continuously decreases to less than 20% of the maximum value at 500 and 600 nm, respectively, and outside of these band limits asymptotically approaches the value null.

At the present time, as far as applicant is aware, there are not known in the art any photoelectric transducers whose spectral sensitivity alone in conjunction with the emission spectrum of useful light sources is capable of producing the desired spectral dependency. Until this is the case it is necessary in order to achieve the desired dependency to insert optical filters in the light path. There can be used for this purpose transmission color filters, for instance a green filter or a high pass-blue filter in combination with a low pass-yellow filter and/or reflection filter.

A particularly advantageous constructional embodiment of measuring apparatus can be constructed according to the invention in such a manner that a portion of the light produced by the light source is delivered to a second photoelectric transducer for forming a reference magnitude. In this way two similar photoresistors or photoconductive cells serving as photoelectric transducers can advantageously form longitudinal branches or arms of an electrical bridge circuit which are parallel to one another, in the transverse or diagonal branch of which there can be electrically connected an indicator instrument for the indication of the hemoglobin content.

In order to use the previously discussed embodment of the invention it is advantageous to carry out the measurement in the following steps:

a. insertion of a hemoglobin-free comparison solution and balancing of the bridge circuit to the indicator value null.
b. insertion of a standard hemoglobin solution and calibration of the measured values indicated therefor.
c. insertion of hemoglobin solutions possessing unknown hemoglobin content.

BRIEF DESCRIPTION OF THE DRAWINGS

The invention will be better understood and objects other than those set forth above, will become apparent when consideration is given to the following detailed description thereof. Such description makes reference to the annexed drawings on the basis of which there will be described in detail hereinafter particular exemplary embodiments of the invention and useful special characteristics of the components thereof, and wherein:

FIG. 1 schematically illustrates the principles of the apparatus construction according to the invention;

FIG. 2 is a graph illustrating the most important characteristics, namely the transducer-sensitivity $I_f$, the sensitivity characteristic $I_{to}$ resulting from the combined action of the spectral-selective components impinged by the light for the comparison solution free of hemoglobin and the basic transmission characteristic $T_H$ of dissolved oxy-hemoglobin $HbO_2$ each in functional dependency upon the light wavelength $\lambda$;

FIG. 3 is a circuit diagram of a linearization measurement or measuring bridge M which can be used in the measuring apparatus:

FIG. 4 is a possible variant embodiment of the arrangement of FIG. 1 with a reflection filter $E_R$ in the light path to the photoelectric transducer F instead of transmission color filters $E_1$, $E_2$;

FIG. 5 is a view looking in the direction of the arrows V—V of FIG. 6, partially in sectional view, of a constructional exemplary embodiment of the invention; and FIG. 6 is a view looking in the direction of the arrows VI—VI of the arrangement of FIG. 5, likewise partially in sectional view, of the same embodiment.

DETAILED DESCRIPTION OF THE PREFERRED EMBODIMENT

Describing now the drawings, in FIG. 1 reference character L designates a suitable light source, preferably a tungsten filament-microincandescent lamp of low power consumption and high longevity. Arranged at the right-hand side of the illustrated lamp L is a photoresistor or photoconductive cell F. In the path of the light or light rays between the lamp L and the photoresistor F there are arranged behind one another an apertured partition or diaphragm B, a small scattering or dispersion plate C, an exchangeable cuvette or vessel D for a hemoglobin solution and two transmission color filters $E_1$, $E_2$, preferably a high pass-blue filter $E_1$ and a low pass-yellow filter $E_2$. The photoresistor F converts the light impinging thereat as a function of the applied voltage into an appropriate current $i_f$. At the left-hand side of the lamp L there is arranged a similar photoresistor F′ which is impinged with a portion of the light produced by the lamp L through the agency of an apertured partition or diaphragm B′ and a small scattering or dispersion plate C′ and generates a reference current $i'_f$.

In FIG. 2 the sensitivity characteristic $I_f$ of the photoresistor F shows the generated current $i_f$ for the wavelengths plotted in the direction of the abscissa for a standard applied voltage during the impingement with light of a predetermined intensity. This characteristic corresponds to the color sensitivity of the human eye, however not to the sensitivity characteristics $I_{to}$ required according to the invention and resulting when using a cuvette or vessel D containing a comparison solution free of hemoglobin and which sensitivity characteristic $I_{to}$ has likewise been illustrated in FIG. 2 in an advantageous and realizable form. On the other hand, such type sensitivity characteristic results with appropriate design of the transmission color filters $E_1$ and $E_2$ inserted according to the arrangement of FIG. 1 in the light path to the photoresistor F in conjunction with the not particularly illustrated emission spectrum of the lamp L and the illustrated sensitivity $I_f$ of the photoresistor F. What is important in this regard is that the resultant sensitivity characteristic $I_{to}$ assumes a maximum approximately at $\lambda = 540$ to $560$ nm and a half-value width (at 50% of the maximum) of at least 60 nm, up to both band limits a residual value of at most 20% of the maximum value, and outside of the band limits asymptotically decreases towards null. Furthermore, there is illustrated in FIG. 2 a transmission characteristic $T_H$ resulting in the case of an oxy-hemoglobin solution when impinged with white light, and for which there is integrally evaluated in a measuring apparatus according to FIG. 1 the section or region located between the band limits $\lambda = 500$ nm and $\lambda = 600$ nm.

In FIG. 3 there is schematically illustrated a linearization measurement or measuring bridge M in which both of the photoresistors F and F′ form two longitudinal branches or arms which are parallel to one another. In the transverse or shunt branch of this bridge M there is connected in circuit a suitable indicator device H for the indication of the desired electrical measurement magnitude, namely a current value or voltage value corresponding to the total hemoglobin content in the cuvette or vessel D. By suitably dimensioning the resistors R and R′ and both of the other longitudinal branches or arms of the measurement bridge or bridge circuit M there can be realized a quasilinear relationship between the current- or voltage value, respectively, indicated by the indicator device H and the hemoglobin concentration in the vessel D within a technologically meaningful range of the hemoglobin content (8 to 24 mg/100 ml). Equally it is possible, if desired while utilizing additional circuit elements, to also render the value of the electrical magnitude indicated at the indicator device H of the linearization-measurement bridge M extensively independent of fluctuations in the brightness of the lamp, so that it is unnecessary to stabilize the lamp brightness.

FIG. 4 illustrates as a variant of the arrangement of FIG. 1 how the desired resultant sensitivity characteristic can be also realized by means of an appropriately constructed reflection filter $E_R$ instead of, as in the arrangement of FIG. 1 with transmission color filters $E_1$, $E_2$, located in the light path from the lamp L to the photoresistor F through the agency of an apertured partition or diaphragm B and a sample-cuvette or vessel D.

FIGS. 5 and 6 illustrate a variant of the principle schematic circuit arrangement of FIG. 1. It will be seen that upon a base plate there are mounted a holder means or device 10, 11 for the lamp L, a holder 12 for the photoresistor or photoconductive cell F, a holder 13 for an apertured partition or diaphragm $B_2$ and for two transmission color filters $E_1$, $E_2$, an exchangeable measurement cuvette or vessel D or a fixedly mounted throughflow-cuvette or vessel, a holder 15 for the apertured partition or diaphragm $B_1$ and the scattering plate or disk C as well as a holder device 16 for the aforedescribed active components F', B', C' of the device for generating the reference magnitudes in front of the photoresistor F'. The entire hemoglobin concentration-measuring apparatus is enclosed by a housing 17 provided with a removable cover 170 for exchanging the vessel or cuvette D.

As a variant of the exemplary embodiments illustrated in FIGS. 1, 5 and 6 of the drawings the components C, $E_1$, $E_2$ and the measurement cuvette D are basically randomly exchangeable with respect to their sequential arrangement. The light losses due to scattering of the light in the measurement vessel or cuvette D can be reduced in that the transducer F is arranged as closely as possible to such cuvette or vessel D and instead the filters $E_1$, $E_2$ are arranged between the light source L and the vessel D.

For the reasons previously mentioned with the disclosed wide-band measurement there can be dispensed with the reaction solution of the cyanmet-technique. This eliminates the need to handle a poisonous substance, shortens the preparatory phase and prevents damage to the leukocytes, which particularly is of importance during the simultaneous counting and especially the volume discrimination of the leukocytes in an automatic counter.

In principle there can be used any hemolyzing not too strongly colored thinning or diluting agent for the determination of the hemoglobin, for instance distilled water.

An advantageously technological technique can be realized from the fact that with the wide-band measurement sufficient light output impinges upon the photoelectric transducers F, F' serving as detectors, so that it is unnecessary to utilize optical focusing elements, with the result that also critical optical adjustments are dispensed with.

From the aforementioned advantages it will be readily apparent that both the preparation of the samples occurs more quickly, simply and inexpensively and also that the expenditure of material is less in the optical portion of the system.

While there is shown and described present preferred embodiments of the invention, it is to be distinctly understood that the invention is not limited thereto, but may be otherwise variously embodied and practiced within the scope of the following claims, Accordingly, what is claimed is:

1. An opto-electrical measuring apparatus for determining the hemoglobin content of a hemoglobin solution through evaluation of its light absorption in a predetermined wavelength range, comprising a light source and a photo-electric transducer arranged in spaced relationship from one another for the insertion therebetween of the hemoglobin solution which is to be illuminated by the light source, additional components arranged in the path of light of the light source, the spectral properties of the light source, the transducer and the additional components arranged in the light path are matched to one another such that in the absence of the hemoglobin solution in the light path an electrical magnitude generated in the photoelectric transducer exhibits a spectral dependency which is a maximum in the wavelength range of approximately 540 to 560 nm and to both sides of said wavelength range with a half-value width of at least 60 nm continually decreases to less than 20% of the maximum value at 500 and 600 nm, respectively, and outside of these band limits asymptotically approaches the value null.

2. The apparatus as defined in claim 1, wherein the emission spectrum of the light source and the spectral sensitivity of the photoelectric transducer collectively produce said spectral dependency.

3. The apparatus as defined in claim 1, wherein said spectral dependency results from the combined effect of the emission spectrum of the light source, the spectral sensitivity of the photoelectric transducer and additional optical filter means inserted in the light path, said additional optical filter means constituting at least part of said further components.

4. The apparatus as defined in claim 3, wherein said additional optical filter means comprises a reflection filter inserted in the light path.

5. The apparatus as defined in claim 3, wherein said additional optical filter means comprises at least one transmission color filter inserted in the light path.

6. The apparatus as defined in claim 1, further including an additional photoelectric transducer, a part of the light produced by the light source is delivered to said additional photoelectric transducer for forming a reference magnitude.

7. The apparatus as defined in claim 6, wherein the two photoresistors are provided as photoelectric transducers which together form parallel longitudinal branches of an electrical bridge circuit having a transverse branch, and an indicator instrument connected in circuit in the transverse branch for the indication of a measurement magnitude representative of the hemoglobin content.

* * * * *